United States Patent [19]

Draper et al.

[11] Patent Number: 5,602,248
[45] Date of Patent: Feb. 11, 1997

[54] PROCESS FOR PREPARATION OF 9α-CHLORO-11β-FORMYLOXYPREGNA-3,20-DIONES

[75] Inventors: Richard W. Draper, North Caldwell; Eugene J. Vater, Lyndhurst, both of N.J.

[73] Assignee: Schering Corporation, Kenilworth, N.J.

[21] Appl. No.: 405,110

[22] Filed: Mar. 16, 1995

[51] Int. Cl.$^6$ .................................................. C07J 75/00
[52] U.S. Cl. ................... 540/61; 540/63; 540/69; 540/70; 540/114; 540/115; 540/116; 540/118; 540/119; 552/564; 552/565; 552/567; 552/568; 552/569; 552/580; 552/581
[58] Field of Search ........................ 552/564, 565, 552/567, 568, 569, 580, 581; 540/61, 63, 69, 70, 114, 115, 116, 118, 119

[56] References Cited

U.S. PATENT DOCUMENTS 4,525,303   6/1985   Takagaki et al. ................. 260/239.55

OTHER PUBLICATIONS

Translation of East German DD 268 954 A1 (1989).

*Primary Examiner*—Kimberly J. Prior
*Attorney, Agent, or Firm*—Henry C. Jeanette

[57] ABSTRACT

Disclosed is a process for producing a compound of the formula:

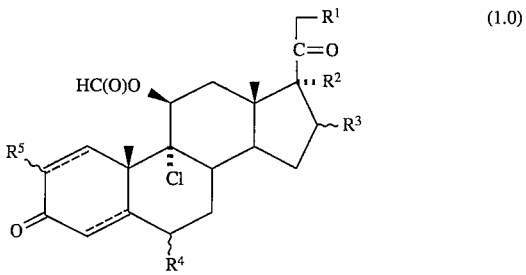

(1.0)

by reacting a compound of the formula:

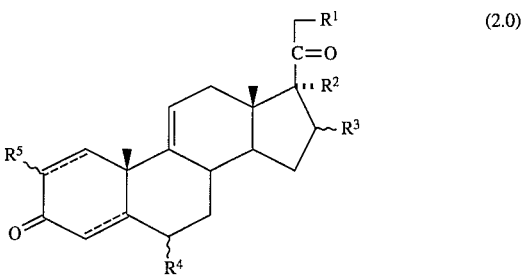

(2.0)

with: (1) a chlorinating reagent selected from an N-chloroimide or an N-chloroamide; (2) an anhydrous strong acid selected from orthophosphoric acid, alkylsulfonic acids, fluoroalkylsulfonic acids or arylsulfonic acids; and (3) anhydrous dimethyl formamide; at a temperature within the range of about −78° to about 0° C., under anhydrous conditions under an inert atmosphere.

31 Claims, No Drawings

PROCESS FOR PREPARATION OF 9α-CHLORO-11β-FORMYLOXYPREGNA-3,20-DIONES

BACKGROUND

A translation of East German 268954 A1 discloses a process for preparing steroids of the pregnane series which contain a 9α-halogen-11β-formyloxy group. Steroids with these substituents are precursors to the respective 9α-halo, 11β-hydroxysteroids. In view of the importance of 9α-halo, 11β-hydroxysteroids, processes which produce their precursors in high yield with a minimum of by-products would be a welcome contribution to the art. The claimed invention provides just such a contribution.

SUMMARY OF THE INVENTION

The claimed invention is directed to a process for producing 9α-chloro-11β-formyloxypregna-3,20-diones from their 9,11 double bond precursors. The use of an anhydrous strong acid, anhydrous reaction conditions and low reaction temperatures produces a 9α-chloro-11β-formyloxypregna-3,20-dione with minimal formation of the 9α,11β-dichloro or 9α-chloro-11β-hydroxy by-products.

The claimed invention is directed to a process for producing a compound of the formula:

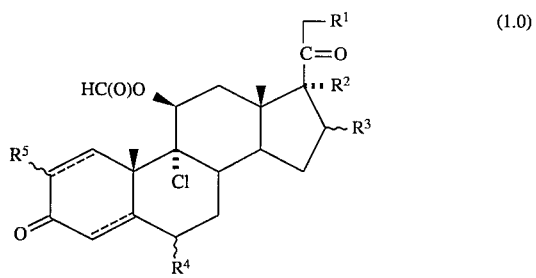  (1.0)

wherein:
the broken lines represent optional bonds;
$R^1$ is selected from H, Cl or F;
$R^2$ is selected from hydroxy or —$OR^6$;
$R^3$ is selected from hydrogen, lower alkyl, or α-$OR^7$; or $R^2$ and $R^3$ taken together represent a 16α,17α-lower alkylidenedioxy having up to 13 carbon atoms;
$R^4$ is selected from hydrogen, α-methyl, α-bromo, α-chloro, α-fluoro, β-fluoro and α-fluoromethyl;
$R^5$ is selected from hydrogen, methyl, fluorine, chlorine and bromine;
$R^6$ is an acyl radical of: (1) a hydrocarbon carboxylic acid having from 2 to 12 carbon atoms (e.g., an alkyl carboxylic acid such as an alkanoic acid); (2) an aromatic carboxylic acid; (3) an arylhydrocarbon carboxylic acid; (4) a heteroaromatic carboxylic acid having at least one oxygen atom in the heteroaryl ring and wherein oxygen is the only heteroatom in the heteroaryl ring (e.g., there are no sulfur or nitrogen atoms in the heteroaryl ring); or (5) a heteroarylhydrocarbon carboxylic acid having at least one oxygen atom in the heteroaryl ring and wherein oxygen is the only heteroatom in the heteroaryl ring (e.g., there are no sulfur or nitrogen atoms in the heteroaryl ring); said acyl radical having 2 to 12 carbon atoms; and
$R^7$ is an acyl radical of a hydrocarbon carboxylic acid having from 2 to 12 carbon atoms;

said process comprising reacting a compound of the formula:

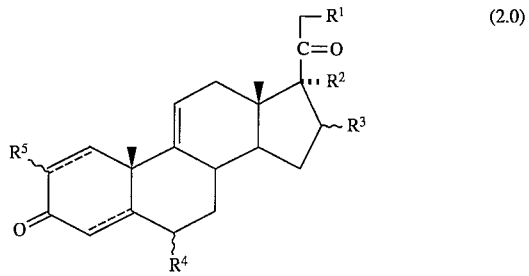  (2.0)

wherein $R^1$, $R^2$, $R^3$, $R^4$, and $R^5$ are as defined above, with: (1) a chlorinating reagent selected from an N-chloroimide or an N-chloroamide; (2) an anhydrous strong acid selected from orthophosphoric acid, alkylsulfonic acids, fluoroalkylsulfonic acids or arylsulfonic acids; and (3) anhydrous dimethylformamide; said reaction being conducted at a temperature within the range of about –78° to about 0° C.; said reaction being conducted under anhydrous conditions; and said reaction being conducted under an inert atmosphere.

DETAILED DESCRIPTION OF THE INVENTION

The terms below, as used herein, have the stated meaning unless otherwise defined herein:

acyl—represents a radical formed from a carboxylic acid, e.g., $$-\overset{O}{\underset{\|}{C}}-R^A$$

wherein $R^A$ represents a saturated hydrocarbon group (e.g., alkyl or cycloalkyl), aryl group, heteroaryl group (wherein the heteroatom or heteroatoms are oxygen), an arylhydrocarbon group or a heteroarylhydrocarbon group (wherein the heteroatom or heteroatoms are oxygen), said acyl group having up to about 12 carbon atoms (e.g., 2 to 12 carbon atoms);

alkyl—represents straight and branched carbon chains and contains from one to twenty carbon atoms, preferably one to six carbon atoms;

anhydrous—means free to substantially free of water;

aromatic (aryl)—represents a carbocyclic group containing from 6 to 12 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, alkoxy, phenoxy, $CF_3$, or —$NO_2$;

cycloalkyl—represents a saturated carbocyclic ring having from 3 to 8 carbon atoms;

DMAP—represents 4-dimethylaminopyridine;

DMF—represents dimethylformamide;

heteroaromatic (heteroaryl)—represents cyclic groups having at least one O atom (i.e., the only heteroatoms are oxygen), and preferably one oxygen atom, interrupting a carbocyclic ring structure and having a sufficient number of delocalized pi electrons to provide aromatic character, with the aromatic heterocyclic groups preferably containing from 2 to 14 carbon atoms, e.g., 2- or 3-furyl; or 2-, 3-, 4-, 5-, 6- or 7-benzofuranyl. Preferred heteroaryl groups are 2- or 3-furyl;

heteroaromatic (heteroaryl) carboxylic acid—represents one of the above defined heteroaryl groups with at least one —COOH group, and preferably one —COOH group;

halogen (halo)—represents Cl, F, Br and I;

hydrocarbon carboxylic acid—represents a straight or branched chain carboxylic acid having from 2 to 12 carbon atoms;

lower alkylidenedioxy—represents an alkylidene group having two oxygen atoms located on two different carbon atoms such that each oxygen atom can form a bond to a different carbon atom on the steroid ring; the alkylidenedioxy group can be generally represented as:

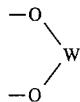

wherein W represents $(CR^B R^C)_n$; $R^B$ and $R^C$ independently represent H, alkyl, and aryl; and n represents 1 to 4 (preferably 1 or 2) such that the total number of carbon atoms in the alkylidenedioxy group is no more than about 13 (e.g., 1 to 13);

lower alkyl—straight or branched chain alkyl groups having from 1 to 6 carbon atoms, e.g., methyl, ethyl, n-propyl, isopropyl, n-butyl, sec-butyl, n-pentyl, isopentyl, n-hexyl, and 2,3-dimethylbutyl; and TEA—represents triethylamine.

The claimed process is carried out under anhydrous conditions and under an inert atmosphere, e.g., nitrogen.

The starting reactant of Formula 2.0 is readily available in the art. A compound of Formula 2.0 is dissolved in anhydrous DMF under an inert atmosphere, e.g., under nitrogen. A sufficient amount of DMF and compound of Formula 2.0 is used to provide the desired amount of 9α-chloro-11β-formyloxypregna-3,20-dione product of Formula 1.0. Usually, about a 0.05 to about a 3 molar solution is made, with about a 0.15 to about a 0.5 molar solution being preferred. Most preferred is about a 0.33 molar solution of the compound of Formula 2.0 in anhydrous DMF.

Preferably, the molar solution is first cooled to about 0° C., then the anhydrous strong acid is added, and then the resulting solution is further cooled to the desired reaction temperature. The reaction is usually carried out at a low temperature, usually about −78° to about 0° C., with about −55° to about −20° C. being preferred, and about −50° C. being most preferred.

About 0.9 to about 2.0 equivalents of the anhydrous strong acid is added, with about 1 equivalent being preferred. Suitable anhydrous strong acids include orthophosphoric acid, alkylsulfonic acids, fluoroalkylsulfonic acids or arylsulfonic acids. Examples of anhydrous alkylsulfonic acids include: methanesulfonic acid, butanesulfonic acid, and camphorsulfonic acid, with methanesulfonic acid being preferred. Examples of anhydrous fluroroalkylsulfonic acids include: trifluoromethanesulfonic acid and perfluorobutanesulfonic acid. Examples of anhydrous arylsulfonic acids include: p-toluenesulfonic acid (p-TSA) and benzenesulfonic acid, with p-toluenesulfonic acid being preferred. Preferably, an alkylsulfonic acid is used and most preferably methanesulfonic acid is used.

A sufficient amount of chlorinating reagent is used to provide the desired amount of 9α-chloro-11β-formyloxypregna-3,20-dione product of Formula 1.0. The chlorinating reagent is generally used in an amount of about 0.8 to about 2.0 equivalents, with about 1 to about 1.05 equivalents being preferred. The chlorinating reagent is added to the mixture of starting reactant, DMF and strong acid. The chlorinating reagent is added over a time period sufficient to maintain the desired reaction temperature. Generally, the chlorinating reagent is added over a time period of about 0.1 to about 1.0 hours. Typically, the chlorinating reagent is added over a time period of about 20 minutes. The chlorinating reagent is an N-chloroimide or an N-chloroamide. Examples of chlorinating reagents include: N-chloroacetamide, N-chlorosuccinimide, 1,3-dichloro-5,5-dimethyhydantoin, or 1,3,5-trichloroisocyanuric acid. Preferably, 1,3-dichloro-5,5-dimethyhydantoin or 1,3,5-trichloroisocyanuric acid is used. Most preferably, 1,3,5-trichloroisocyanuric acid, i.e.,

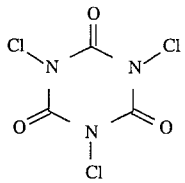

is used.

The reaction mixture (starting reactant of Formula 2.0, DMF, strong acid and chlorinating reagent) is stirred at the desired reaction temperature for a time period sufficient to result in the consumption of the starting reactant. Generally, the reaction mixture is stirred, i.e., the reaction takes place, over a time period of about 1 to about 48 hours, with about 16 to about 40 hours being preferred, and about 20 to about 30 hours being most preferred.

The final product, i.e., a compound of Formula 1.0 or 1.1, if desired, can be separated from the reaction mixture and purified by techniques well known to those skilled in the art. For example, a sufficient amount of deionized water or 10% aqueous sodium sulfite is added to the reaction mixture to cause precipitation of the final product. Typically, the final product is then filtered off, washed with water and dried. Alternatively, after adding the deionized water or sodium sulfite solution, the product can be extracted into a suitable organic solvent (such as, for example, methylene chloride or ethyl acetate), washed with water and concentrated to recover the final steroid product of Formula 1.0 or 1.1. The final product can optionally be purified by crystallization following procedures well known in the art.

$R^1$ is preferably Cl.

Preferably, $R^2$ is —OH or —$OR^6$ wherein $R^6$ is an acyl radical of a hydrocarbon, aromatic or heteroaromatic carboxylic acid.

$R^2$ is most preferably hydroxy (—OH) or —$OR^6$ wherein $R^6$ is an acyl radical of a heteroaromatic carboxylic acid. Even more preferably, $R^2$ is —OH. Examples of heteroaromatic carboxylic acids include: 2-furancarboxylic acid; 3-furancarboxylic acid; 5-bromo-2-furancarboxylic acid; 2-benzofurancarboxylic acid; and 3-benzofurancarboxylic acid. The preferred heteroaromatic carboxylic acid is 2-furancarboxylic acid. Thus, $R^2$ is preferably —OH or —$OR^6$ wherein $R^6$ is the acyl radical of 2-furancarboxylic acid, i.e., $R^6$ is

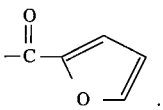

$R^2$, as stated above, can be —$OR^6$ wherein $R^6$ is the acyl radical of a hydrocarbon carboxylic acid or $R^6$ is the acyl radical of an aromatic carboxylic acid. Hydrocarbon carboxylic acids include the alkanoic acids exemplified by acetic, propionic, trimethylacetic, butyric, isobutyric, valeric, isovaleric, caproic, tert-butylacetic, enanthic, caprylic, cyclopentyl-propionic, and adamantanecarboxylic acids. Hydrocarbon carboxylic acids also include the substituted alkanoic acids such as phenoxyacetic and β-chloropropionic acids.

Aromatic carboxylic acids for $R^6$ include substituted aromatic acids. Examples of aromatic carboxylic acids include: benzoic, toluic, p-chloro-benzoic, p-fluorobenzoic, p-methoxybenzoic, and 3',5'-dimethylbenzoic acids.

Arylhydrocarbon carboxylic acids for $R^6$ refers to hydrocarbon carboxylic acids substituted with an aryl group (e.g., arylalkanoic acids). Examples of arylhydrocarbon carboxylic acids include: phenylacetic, phenylpropionic, and β-benzoylaminoisobutyric acids.

Heteroarylhydrocarbon carboxylic acids for $R^6$ refers to hydrocarbon carboxylic acids substituted with an aryl group (e.g., heteroarylalkanoic acids). Examples of heteroarylhydrocarbon carboxylic acids include: 2-furanacetic acid and 3-furanpropionic acid.

The lower alkylidene groups of the alkylidenedioxy of the $R^3$ substituent represent hydrocarbon radicals having 1 to 13 carbon atoms. Examples of lower alkylidene groups include methylene, ethylidene, n-propylidene, isopropylidene, n-butylidene, and sec-butylidene.

Preferably, $R^3$ represents H, lower alkyl, or α-$OR^7$. More preferably, $R^3$ is a lower alkyl group, and most preferably $R^3$ is methyl. For example $R^3$ can be α-methyl or β-methyl, with α-methyl being preferred. The hydrocarbon carboxylic acids for $R^7$ are as defined for the hydrocarbon carboxylic acids of $R^6$.

Preferably, $R^4$ and $R^5$ are both hydrogen.

The compounds produced by the claimed process can be further reacted with reagents by processes known in the art to produce a variety of 9α-chloro-11β-hydroxypregna-3,20-diones. For example, preferably the compound of Formula 3.0:

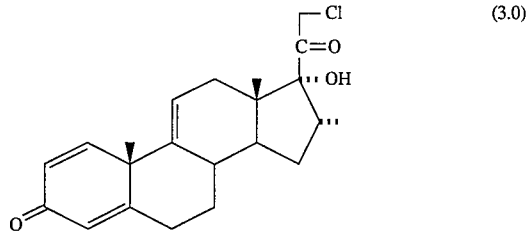

reacted with 1,3,5-trichloroisocyanuric acid, CH3SO₃H (methanesulfonic acid) and DMF according to the process of the invention produces a compound of Formula 4.0:

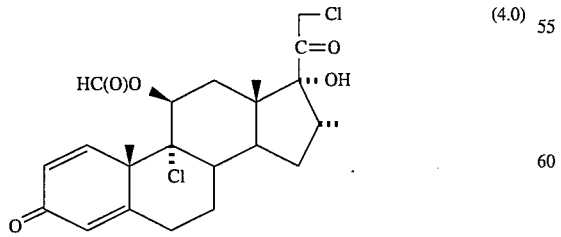

Using known techniques, Compound 4.0 can then be reacted with furoyl chloride, a tertiary organic base (e.g., TEA), and optionally a catalyst such as DMAP, in methylene chloride to produce a compound of Formula 5.0:

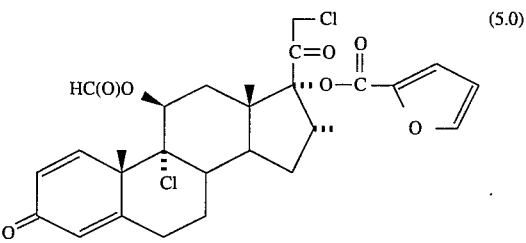

Again, using known techniques, the compound of Formula 5.0 can be reacted with a mixture of $NH_4OH$, methanol and water to hydrolyze the 11β-formyloxy group to produce to 11β-hydroxy compound of Formula 5.1:

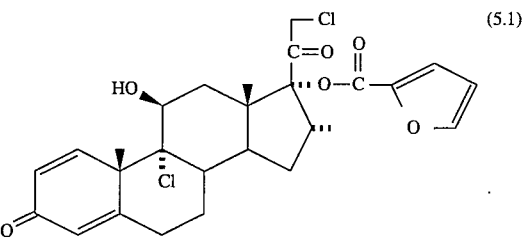

In an alternative reaction scheme, the compound of Formula 7.0:

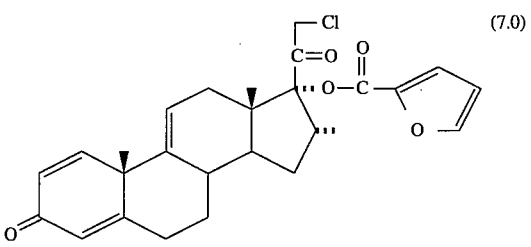

reacted with 1,3,5-trichloroisocyanuric acid, $CH_3SO_3H$ (methanesulfonic acid) and DMF according to the process of the invention produces a compound of Formula 5.0. The compound of Formula 5.0 is then hydrolyzed, as described above, to the compound of Formula 5.1.

Compounds of Formulas 3.0 and 7.0 can be produced by techniques well known in the art. The compound of Formula 5.1 and similar compounds are described in U.S. Pat. No. 4,472,393, the disclosure of which is incorporated herein by reference thereto.

The examples that follow are intended to exemplify the claimed invention, and such examples should not be construed as limiting the disclosure or the claimed invention.

In the examples that follow, certain compounds were identified by comparing their HPLC retention times with the HPLC retention times of compounds whose structures were confirmed by NMR and Mass Spectroscopy (MS)—i.e., standards. The data are:

(A) Compound of Formula 4.0:
  (1) MS: $MH^+$455.0 and $(M+2)H^+$457.1 (Abundance 3/2);
  (2) NMR: δ 8.36 (1H, s), 6.83 (1H, d), 6.27 (1H, d), 6.04 (1H, s), 5.51 (1H, s), 5.49 (1H, bs), 4.78 (1H, d), and 4.49 (1H, d);

(B) Compound of Formula 4.1:
  (1) MS: $MH^+$445.2 (Abundance=1) and $(M+2)H^+$447.2 (Abundance=1);
  (2) NMR: δ 7.27 (1H, d), 6.27 (1H, d), 5.99 (1H, s), 5.53 (1H, s), 4.99 (1H, wd), 4.76 (1H, d), and 4.49 (1H, d);

(C) Mixture of the compounds of Formulas 5.0 and 9.0:
  (1) MS: (a) from Formula 5.0: MH$^+$549.4 (Abundance= 3) and (M+2)H$^+$551.4 (Abundance=2); and from Formula 9.0: MH$^+$643 and (M+2)H$^+$645;
  (2) NMR: δ 8.38 (1H, s), 8.03 (1H, s), 7.27 (1H, d), 6.87 (1H, d), 6.72 (1H, d), 6.30 (1H, d), 6.06 (1H, s), 5.56 (1H, bs), and 4.60 (2H, q);

(D) Compound of Formula 5.2:
  (1) MS: MH$^+$539 and (M+2)H$^+$541 (Relative Abundance 100/92)
  (2) NMR: δ 8.02 (1H, s), 7.24 (1H, d), 7.21 (1H, d), 6.69 (1H, d), 6.25 (1H, d), 6.00 (1H, d), 5.04 (1H, d), and 4.58 (2H, bm).

EXAMPLE 1

9α,21-dichloro-11β,17α-dihydroxy-16α-methylpregna-1,4-diene-3,20-dione 11-formate

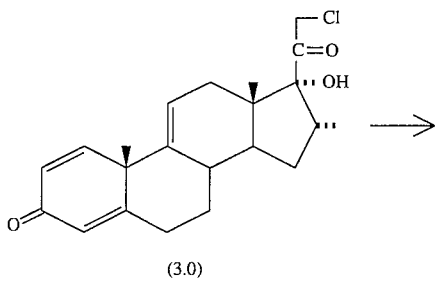

(3.0)

21-chloro-17α-hydroxy-16α-methylpregna-1,4,9$^{(11)}$-triene -3,20-dione (Formula 3.0, 11.22 g, 30 mmole) and dry dimethylformamide (90 ml) were added to a dry flask. The solution was blanketed with nitrogen and cooled to about 0° C. with an ice bath. While stirring, methanesulfonic acid (1.966 ml, 30 mmole) was added dropwise. The resulting solution was cooled to about –55° C. The solution was stirred as 1,3,5-trichloroisocyanuric acid (2.40 g, 10 mmole) was added in portions over 30 minutes. After 18¼ hours, additional 1,3,5-trichloroisocyanuric acid (0.121 g, 0.5 mmole) was added. After 37½ hours the reaction was warmed to about 0° C. and water (250 ml) was slowly added. The precipitate was filtered off, washed well with water, and dried to a constant weight in an oven at 60° C. The product (Formula 4.0) was obtained in a yield of 13.93 g.

Samples were taken from the above reaction and analyzed by HPLC after 12, 17, 20½, and 37½ hours. For the HPLC analysis the solvent used was acetonitrile/water in a 60:40 ratio, the flow rate was 1.5 ml/minute, the column was a Waters $C_{18}\mu$ Bondapak and detection was by UV@254 nm. The data given in Table 1 is area %. The dashed lines ( - - - ) in the Table mean that the peak height was insufficient for integration.

TABLE 1

| Time (hours) | 9α-chloro-11β-formate (product of Formula 4.0) | 9α, 11β-dichloro (by-product of Formula 4.1) | Starting Material |
| --- | --- | --- | --- |
| 12 | 92.9 | 0.1 | 6.7 |
| 17 | 94.9 | — | 4.8 |
| 20½ | 99.0 | 0.1 | 0.7 |
| 37½ | 99.7 | — | — |

The compound of Formula 4.1 has the structure:

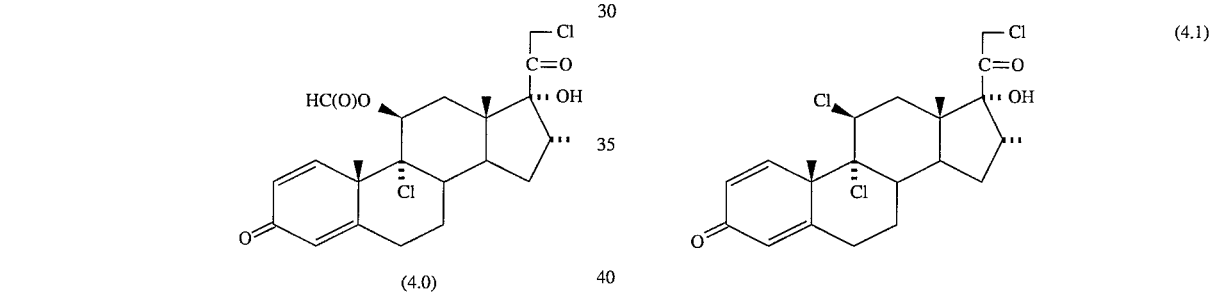

EXAMPLE 2

9α,21-dichloro-11β,17α--dihydroxy-16α-methylpregna-1,4-diene-3,20-dione-11-formate-17-(2'-furoate) (Formula 5.0) and 9α,21-dichloro-11β,17α,20-trihydroxy-16α-methylpregna-1,4,20-trien-3-one -11-formate-17,21-(di-2'-furoate) (Formula 9.0)

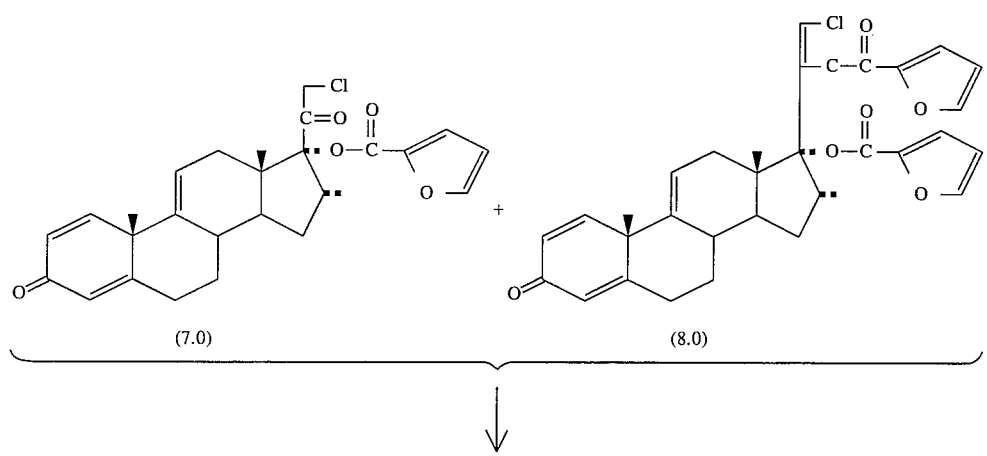

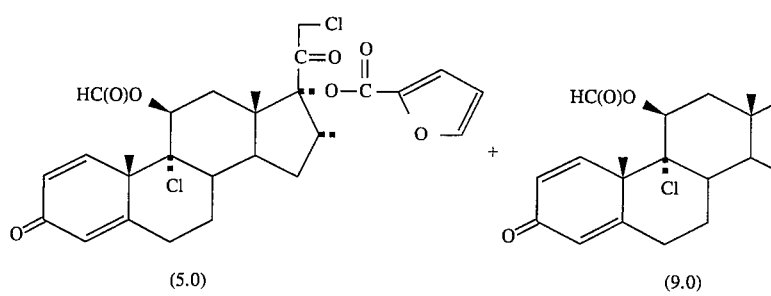

(5.0)           (9.0)

A mixture of 21-chloro-17α-hydroxy-16α-methylpregna-1,4,9(11)-triene-3,20-dione-17-(2'-furoate) (Formula 7.0) and 21-chloro-17α,20-dihydroxy-16α-methylpregna-1,4,9(11),20-tetraen-3-one-17,20-(di-2'-furoate) (Formula 8.0) (0.374 g, ratio 90.5:7.5 by HPLC area % of Formula 7.0 to Formula 8.0), and dry dimethylformamide (3 ml) was added to a dry flask. The solution was blanketed with nitrogen and cooled to about 0° C. with an ice bath. Methanesulfonic acid (0.0655 ml, 1.0 mmole) was added dropwise with stirring to the mixture. The resulting mixture was cooled to −25° C. and 1,3-dichloro-5,5-dimethyhydantoin (0.197 g, 1.0 mmole) was added in portions over a time period of 15 minutes. The reaction mixture was stirred for 26 hours at −25° C. The reaction mixture was then warmed to room temperature, water was added dropwise with stirring, and the precipitate formed was extracted with methylene chloride. The extracts were washed with brine, dried over sodium sulfate, and then concentrated to give the products.

Samples were taken from the above reaction and analyzed by HPLC after 2.5, 4.75 and 26 hours. For the HPLC analysis the solvent used was acetonitrile/water in a 60:40 ratio, the flow rate was 1.5 ml/minute, the column was a Waters $C_{18}\mu$ Bondapak and detection was by UV@254 nm. The data given in Table 2 is area %. The dashed lines ( - - - ) in the Table means that the peak height was insufficient for integration.

TABLE 2

| Time (hours) | monofuroate 9α-chloro-11β-formate (product of Formula 5.0) | difuroate 9α-chloro-11β-formate (by-product of Formula 9.0) | monofuroate 9α,11β-dichloro (by-product of Formula 5.2) |
|---|---|---|---|
| 2.5 | 87.8 | 8.8 | 0.5 |
| 4.75 | 85.0 | 7.3 | — |
| 26 | 85.6 | 7.7 | 0.7 |

The compound of Formula 5.2 has the structure:

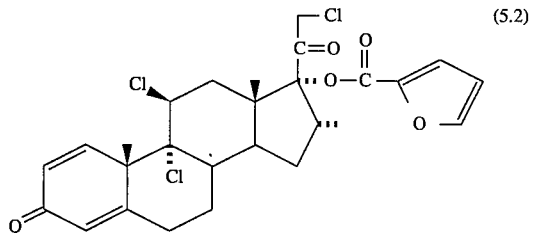

(5.2)

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A process for producing a compound of the formula:

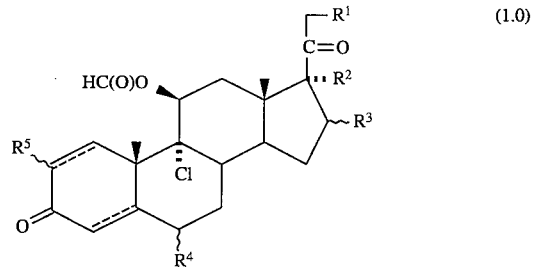

(1.0)

wherein:

the broken lines represent optional bonds;

$R^1$ is selected from H, Cl or F;

$R^2$ is selected from hydroxy or —$OR^6$;

$R^3$ is selected from hydrogen, lower alkyl, or α-$OR^7$; or $R^2$ and $R^3$ taken together represent a 16α,17α-lower alkylidenedioxy having up to 13 carbon atoms;

$R^4$ is selected from hydrogen, α-methyl, α-bromo, α-chloro, α-fluoro, β-fluoro and α-fluoromethyl;

$R^5$ is selected from hydrogen, methyl, fluorine, chlorine and bromine;

$R^6$ is an acyl radical of: (1) a hydrocarbon carboxylic acid having from 2 to 12 carbon atoms; (2) an aromatic carboxylic acid wherein said aromatic group contains from 6 to 12 carbon atoms; (3) an arylhydrocarbon carboxylic acid wherein said aryl group contains from 6 to 12 carbon atoms, and said hydrocarbon carboxylic acid group represents a straight or branched chain carboxylic acid having from 2 to 12 carbon atoms; (4) a heteroaromatic carboxylic acid having at least one oxygen atom in the heteroaryl ring and wherein oxygen is the only heteroatom in the heteroaryl ring, and wherein the aromatic heterocyclic group contains from 2 to 14 carbon atoms; or (5) a heteroarylhydrocarbon carboxylic acid having at least one oxygen atom in the heteroaryl ring and wherein oxygen is the only heteroatom in the heteroaryl ring, and wherein the aromatic heterocyclic group contains from 2 to 14 carbon atoms, and said hydrocarbon carboxylic acid group represents a straight or branched chain carboxylic acid having from 2 to 12 carbon atoms; said acyl radical having from 2 to 12 carbon atoms; and $R^7$ is an acyl radical of a hydrocarbon carboxylic acid having from 2 to 12 carbon atoms;

said process comprising reacting, under anhydrous conditions and under an inert atmosphere, a compound of the formula:

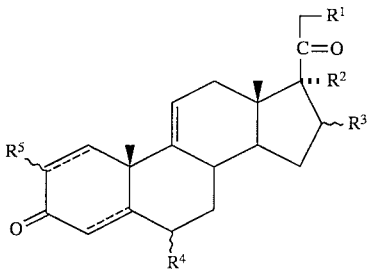

wherein $R^1$, $R^2$, $R^3$, $R^4$, and $R5$ are as defined above, with: (1) a chlorinating reagent selected from an N-chloroimide or an N-chloroamide; (2) an anhydrous strong acid selected from orthophosphoric acid, alkylsulfonic acids, fluoroalkylsulfonic acids or arylsulfonic acids; and (3) anhydrous dimethylformamide; said reaction being conducted at a temperature within the range of about −78° to about 0° C.

2. The process of claim 1 wherein said chlorinating reagent is selected from N-chloroacetamide; N-chlorosuccinimide; 1,3-dichloro-5,5-dimethyhydantoin; or 1,3,5-trichloroisocyanuric acid.

3. The process of claim 2 wherein said chlorinating reagent is selected from 1,3-dichloro-5,5-dimethyhydantoin or 1,3,5-trichloroisocyanuric acid.

4. The process of claim 3 wherein said chlorinating reagent is 1,3,5-trichloroisocyanuric acid.

5. The process of claim 1 wherein said acid is an alkylsulfonic acid.

6. The process of claim 5 wherein said acid is methanesulfonic acid.

7. The process of claim 1 wherein said temperature is within the range of about −55° C. to about −20° C.

8. The process of claim 7 wherein said temperature is about −50° C.

9. The process of claim 1 wherein both of said optional double bonds are present.

10. The process of claim 1 wherein $R^1$ is Cl, and $R^2$ is selected from hydroxy or —$OR^6$ wherein $R^6$ is an acyl radical of a heteroaromatic carboxylic acid.

11. The process of claim 10 wherein $R^2$ is selected from hydroxy or

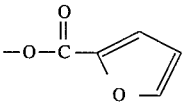

12. The process of claim 1 wherein $R^3$ is selected from H, α-$OR^7$ or a lower alkyl.

13. The process of claim 12 wherein $R^3$ is a lower alkyl.

14. The process of claim 13 wherein $R^3$ is methyl.

15. The process of claim 1 wherein $R^4$ and $R^5$ are hydrogen.

16. The process of claim 1 wherein said chlorinating reagent is selected from 1,3-dichloro-5,5-dimethyhydantoin or 1,3,5-trichloroisocyanuric acid; said acid is an alkylsulfonic acid; and said temperature is within the range of about −55° to about −20° C.

17. The process of claim 16 wherein said chlorinating reagent is 1,3,5-trichloroisocyanuric acid, and said alkylsulfonic acid is methanesulfonic acid.

18. The process of claim 17 wherein both optional double bonds are present; $R^2$ is selected from hydroxy or —$OR^6$ wherein $R^6$ is an acyl radical of a heteroaromatic carboxylic acid; and $R^3$ is selected from H, α-$OR^7$ or a lower alkyl.

19. The process of claim 18 wherein $R^2$ is hydroxy or

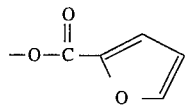

20. The process of claim 19 wherein $R^3$ is lower alkyl.

21. The process of claim 20 wherein $R^1$ is Cl and $R^3$ is methyl.

22. The process of claim 21 wherein $R^2$ is

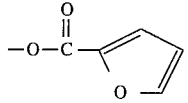

23. The process of claim 1 wherein said inert atmosphere is nitrogen.

24. A process for producing a compound of the formula:

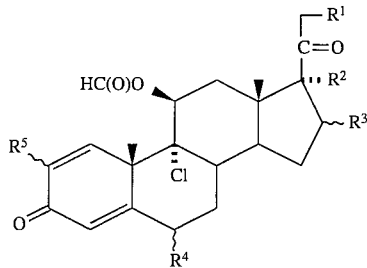

wherein:

$R^1$ is selected from H, Cl or F;

$R^2$ is selected from hydroxy or —$OR^6$;

$R^3$ is selected from hydrogen, lower alkyl, or α-$OR^7$; or $R^2$ and $R^3$ taken together represent a 16α,17α-lower alkylidenedioxy having up to 13 carbon atoms;

$R^4$ is selected from hydrogen, α-methyl, α-bromo, α-chloro, α-fluoro, β-fluoro and α-fluoromethyl;

$R^5$ is selected from hydrogen, methyl, fluorine, chlorine and bromine;

$R^6$ is an acyl radical of: (1) a hydrocarbon carboxylic acid having from 2 to 12 carbon atoms; (2) an aromatic carboxylic acid wherein said aromatic group contains from 6 to 12 carbon atoms; (3) an arylhydrocarbon carboxylic acid wherein said aryl group contains from 6 to 12 carbon atoms, and said hydrocarbon carboxylic acid group represents a straight or branched chain carboxylic acid having from 2 to 12 carbon atoms; (4) a heteroaromatic carboxylic acid having at least one oxygen atom in the heteroaryl ring and wherein oxygen is the only heteroatom in the heteroaryl ring, and wherein the aromatic heterocyclic group contains from 2 to 14 carbon atoms; or (5) a heteroarylhydrocarbon carboxylic acid having at least one oxygen atom in the heteroaryl ring and wherein oxygen is the only heteroatom in the heteroaryl ring, and wherein the aromatic heterocyclic group contains from 2 to 14 carbon atoms, and said hydrocarbon carboxylic acid group represents a straight or branched chain carboxylic acid having from 2 to 12 carbon atoms; said acyl radical having from 2 to 12 carbon atoms; and $R^7$ is an acyl radical of a hydrocarbon carboxylic acid having from 2 to 12 carbon atoms;

said process comprising reacting, under anhydrous conditions and under an inert atmosphere, a compound of the formula:

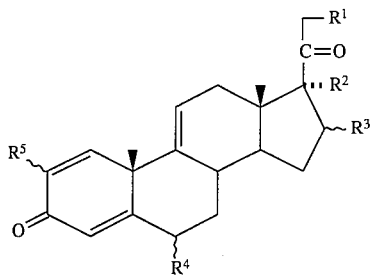 (2.1)

wherein $R^1$, $R^2$, $R^3$, $R^4$, and $R^5$ are as defined above, with: (1) from about 1 to about 1.05 equivalents of a chlorinating reagent selected from N-chloroacetamide, N-chlorosuccinimide, 1,3-dichloro-5,5-dimethy-hydantoin, or 1,3,5-trichloroisocyanuric acid; (2) about 1 equivalent of an anhydrous strong acid selected from orthophosphoric acid, alkylsulfonic acids, fluoroalkylsulfonic acids or arylsulfonic acids; and (3) anhydrous dimethylformamide; wherein said compound of formula 2.1 is dissolved in said anhydrous dimethylformamide to produce about a 0.15 to about a 0.5 molar solution; the reaction being conducted at a temperature within the range of about −78° to about 0° C.

25. The process of claim 24 wherein said chlorinating reagent is 1,3,5-trichloroisocyanuric acid; said acid is methanesulfonic acid; and said reaction being conducted at a temperature within the range of about −55° to about −20° C.

26. The process of claim 25 wherein $R^1$ is Cl; $R^2$ is selected from hydroxy or $-OR^6$ wherein $R^6$ is an acyl radical of a heteroaromatic carboxylic acid; and $R^3$ is selected from H, α-$OR^7$ or a lower alkyl.

27. The process of claim 26 wherein $R^1$ is Cl; $R^2$ is selected from hydroxy or

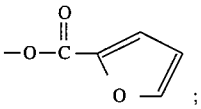 ;

and $R^3$ is lower alkyl.

28. The process of claim 27 wherein $R^3$ is α-methyl; $R^4$ is hydrogen; and $R^5$ is hydrogen.

29. The process of claim 28 wherein $R^2$ is

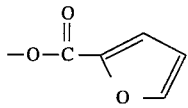 .

30. The process of claim 28 wherein said inert atmosphere is nitrogen.

31. The process of claim 24 wherein said inert atmosphere is nitrogen.

* * * * *